(12) United States Patent
Auchincloss

(10) Patent No.: US 6,346,275 B1
(45) Date of Patent: Feb. 12, 2002

(54) CALCAREOUS MATERIAL

(75) Inventor: Leslie Auchincloss, Channel Islands (GB)

(73) Assignee: Aquacal Limited (IE)

(*) Notice: Subject to any disclaimer, the term of this patent is extended or adjusted under 35 U.S.C. 154(b) by 0 days.

(21) Appl. No.: 09/355,606

(22) PCT Filed: Feb. 3, 1998

(86) PCT No.: PCT/IB98/00142

§ 371 Date: Sep. 14, 1999

§ 102(e) Date: Sep. 14, 1999

(87) PCT Pub. No.: WO98/33508

PCT Pub. Date: Aug. 6, 1998

(30) Foreign Application Priority Data

Feb. 3, 1997 (GB) .............................................. 9702130

(51) Int. Cl.[7] .............................................. A61K 35/80
(52) U.S. Cl. ........................ 424/520; 426/74; 426/648
(58) Field of Search ........................ 424/520; 426/74, 426/648

(56) References Cited

FOREIGN PATENT DOCUMENTS

| | | |
|---|---|---|
| BE | 693094 | 7/1967 |
| DE | 2947186 | 5/1981 |
| EP | 0308329 | 3/1989 |
| FR | 2201040 | 4/1974 |
| FR | 2674126 | 9/1992 |
| GB | 1113318 | 5/1968 |
| WO | 8501655 | 4/1985 |
| WO | 9211020 | 7/1992 |

OTHER PUBLICATIONS

Chemical Patents Index, Documentation Abstracts Journal, Derwent Publications, London 1993, Nr. 93–111855/14; JP405049446.

Oceanis vol. 15 Part 5 Ppr 693: Abstract of Institute of Oceanography Report on Corallinaceae, 1989.

*Primary Examiner*—Herbert J. Lilling
(74) *Attorney, Agent, or Firm*—Ladas and Parry (57) ABSTRACT

Calcareous materials which are very purified residues of corallinaceae particulary Lithothamnium corallioides have unusual therapeutic properties including treatment of conditions created by failure of immune regulation, for example rheumatoid or osteo arthritis, osteoporosis and other conditions involving pH control. A method for purification is provided. Also provided are compositions of the residues together with fatty acids, glycerides, polyglycols and emulsifiers. Particularly advantageous are compositions of the residues and medium chain triglycerides.

28 Claims, 6 Drawing Sheets

CALCAREOUS MATERIAL

FIELD OF INVENTION

This invention relates to calcareous materials from natural organic sources and particularly compositions comprising residues of corallinaceae for example Lithothamnium corallioides for use in the therapeutic treatment of humans or animals. The invention also relates to the use of said materials in foodstuffs and processing of foodstuffs.

BACKGROUND OF INVENTION

Corallinaceae, for example Lithothamnium corallioides, are known seaweeds which are very abundant in certain cold and temperate seas. Once harvested the crude residual product consists primarily of mineral substances, particularly calcium carbonate and magnesium carbonate. The largest component is calcium carbonate, often about 34% by weight. This product is sometimes identified as Maërl though the term Maërl encompasses residues of coralline algae of various members of the order corallinales (Class Rhodophyceae) including members of corallinaceae for example members of the species Lithothamnium corallioides, Phymatolithon calcareum and Lithothamnium glaciate.

Crude corallinaceae (Lithothamnium corallioides) residues have been commercially available for use in the prevention of acidosis in intensively fed cows. In French patent FP2 201 040 there is disclosed the use of Maërl which appears to be in the crude form for animal feeds. Such products as have been available until the present time have tended to be relatively impure products frequently from contaminated sources. Usually they contain significant amounts of siliceous materials derived from the original product as dredged and other non-corallinaceae residues for example ground shells of sea-creatures.

The Institute of Oceanography in Paris produced a report on corallinaceae particularly Lithothamnium in 1989 describing the residual crude product (Maërl) and describing its use in treatment of soil and for animal feed as a dietary supplement and for treatment of water.

The subject invention provides further medical uses for compositions comprising residue of corallinaceae (Maërl) in highly purified form.

SUMMARY OF INVENTION

Corallinaceae particularly Lithothamnium corallioides are coralline algae. There are a number of sub-species of corallinaceae particularly Lithothamnium differentiated by morphological data but these data can vary depending on local sea bed and weather conditions. Other known "relatives" include Phymatolithon calcareum and in more northerly regions Lithothamnium glaciale. These plants lay down calcium carbonate in their cell walls which gives them a hard stony texture. The living corallinaceae for example Lithothamnium corallioides generally show a red colour due to the presence of a pigment phycoerythrin in their structure. When dead the colour is white or yellowish. Corallinaceae for example Lithothamnium corallioides occurs naturally in cold and temperate seas and has been reported in Norway, Canada, Scotland, Ireland and France.

Since compositions of the subject invention are to be used therapeutically it is of course important that the corallinaceae which is to be exploited in the invention is derived from a part of the world which does not suffer from heavy pollution. For this purpose corallinaceae particularly Lithothamnium corallioides harvested from stocks north of Lonehort Point, Castletownbere, County Cork in the Republic of Ireland have proved very satisfactory but there are also deposits off the West Coast of Galway.

In the concentrated and purified form of the invention the residue of corallinaceae has proved particularly effective for use in a composition for the manufacture of medicament for the treatment of disorders arising from immunoregulation problems. These problems are, for example, rheumatoid arthritis, osteo arthritis, gout, raised cholesterol levels, period pains, reduced body fluid pH levels, osteoporosis, incipient ulcerative conditions, and certain conditions sometimes described as "low energy" or chronic fatigue problems. Also the product is applicable to reduced calcium level problems and raised pH levels in the colon and certain indigestion problems.

Naturally occurring residues of Lithothamnium corallioides were harvested at the above site at Lonehort Point, purified, concentrated and formed into capsules containing 0.5 grammes of concentrate.

The raw material can be purified by initial extensive washing with sea and fresh water together with removal of extraneous sand, shells, and other debris particularly siliceous debris such as stones. This step usually reduces the material obtained by dredging from the sea bed to about 20% by weight.

The cleaned and separated product is then subjected to intensive cleaning by for example, bleaching and sterilising in hydrogen peroxide for from 8 to 24 hours, further washing in water, drying in a sterile fluid bed and final milling under bacterial controlled conditions.

The stringent washing conditions reduce sodium content of the raw product from amounts in the order of well in excess of 1,000 ppm for example amounts up to 5,200 ppm to sodium contents in the low hundreds, for example 300 ppm. Thus there is a reduction of about 10 fold in the sodium content as compared to raw material.

The silica content of this final material is normally not more than 0.5% by weight as compared to a silica content in previously available Maërl from a commercial source, of about 5% by weight.

The product is packaged by aseptic formation into capsules, tablets or emulsions.

A representative sample of this purified, concentrate contained the following elements in the following amounts

| | |
|---|---|
| Calcium | 34% |
| Magnesium | 2.4% |
| Phosphorous | 0.08% |
| Potassium | 0.10% |
| Sulphur | 0.45% |
| Iron | 20 ppm |
| Boron | 16.5 ppm |
| Sodium | 300 ppm |

-continued

| | |
|---|---|
| Manganese | 125 ppm |
| Cobalt | 6 ppm |
| Copper | 10 ppm |
| Zinc | 37 ppm |
| Selenium | 1 ppm |
| Molybdenum | <3 ppm |
| Iodine | 160 ppm |
| Arsenic | <1 ppm |
| Lead | <1 ppm |
| Chromium | 13 ppm |
| Cadmium | 0.2 ppm |
| Mercury | <50 ppb |
| Aluminium | <1 ppm |

One possible reason for the activity of this material is the availability of mineral elements. These serve the physiology of the body in various ways for example;

(a) constituents of skeletal structure;

(b) regulation of physical properties of colloidal systems (viscosity, diffusion, osmotic pressure);

(c) acid-base regulators; and (d) components and activators of enzymes and other active biological systems.

Thus the calcium from the product of the invention may assist in:

(i) blood coagulation;

(ii) muscle irritability;

(iii) myocordial function;

(iv) control of acetylcholine (neuromuscular irritability); and (v) enzyme activation The magnesium content may be of benefit in relation to over 300 enzymatic reactions including carbohydrate utilisation, ATP metabolism, muscle contraction, nerve impulse conduction, transmembrane ion transport, enzyme activation particularly in relation to utilisation of vitamins B1, B2, B6, C and E, and synthesis of fat, protein and nucleic acids. The composition may assist in providing an Na/calcium balance and also may affect the potassium balance. In addition the content and availability of metals such as copper, iron, cobalt, zinc and other components in the product may have effects on physiological and biochemical systems in the body which would not have been anticipated from the mere analysis of the raw material. For example, the copper content may assist with connective tissue dysfunctions, bone fragility, cardiovascular disorders and defects in the lysyl oxidase function. The zinc content may assist with defects in the over 70 enzymatic systems in which zinc is a cofactor.

Rat feeding trials have been conducted with the concentrate to assess the safety of the product in humans. These trials were completely satisfactory.

Pharmaceutically effective amount of the corallinaceae residues can be used in the methods of the invention.

For example patients being treated with the concentrate can be dosed with from 0.5 grammes to 3 grammes of concentrate per day.

Compositions comprising effective amounts of the purified concentrate are useful inter alia for the treatment of conditions involving failure of immuno regulations and include rheumatoid and osteo arthritis, gout, high cholesterol, period pains, low body fluid pH, osteoporosis, and incipient ulcerative conditions of the type which have been successfully treated with antiulcer drugs (such as Tagamet, Zantex, Losec (all are Registered Trade Marks)). An important aspect is treatment of chronic fatigue problems and the achieving of a feel good factor.

Such compositions can also be used for the treatment of indigestion. Furthermore such compositions can be used to treat low calcium levels. A dosage of three 0.5 gramme capsules per day supplies 480 milli-grammes a day of calcium to the patient.

Furthermore such compositions can be used to treat ulcerative conditions of the colon. It is theorised that such treatments result in elevation of colon pH and subsequent suppression of *Heliobacter pylori*.

Such compositions have also been effective in treating hangovers.

Another aspect of the invention is the combination of the purified residues of corallinaceae with fatty acids or polyols. The unusually porous structure of the Corallinaceae product which will hereinafter for convenience be referred to as the Calcium Product is advantageous over other natural calcium sources in allowing the absorption of fatty acids and glycerides as well as polyols to allow a product which is still flowable.

In particular the calcium product is advantageous when combined with functional polyunsaturated fatty acids (PUFAs) also known as omega-long-chain-fatty acids (LCFAs). These fatty acids are of growing interest in the fortification of food formulae particularly those for children.

According to the invention there is provided a composition comprising the combination of a residue in very pure form of a corallinaceae (Maërl) and a fatty acid, a glyceride or a polyglycol.

There is also provided a composition comprising the combination of a residue in very pure form of corrallinaceae (Maërl) and an emulsifier.

There is further provided a method of forming emulsions in the manufacture of foods wherein an emulsifier is combined with a residue in very pure form of corrallinaceae (Maërl) and simultaneously or subsequently with an oil phase of a food stuff and thereafter an emulsion is formed with an aqueous phase.

Omega-LCFAs are divided into two families:

Omega-6: ARA (arachidonic acid) from plant and animal fats.

Omega-3: EPA (Eicosapentaenoic acid) and DHA (docosahexaenoic acid) from fish oils and algae.

ETA (Eicosatetraenoic acids) extracted from the New Zealand Green-Lipped Mussels (Perna Canalicus).

The omega-3 family has been shown to be essential for normal biological functions. EPA plays an important role in the regulation of inflammatory immune reactions and blood pressure: it is a precursor of prostaglandin E3 that inhibits blood clots.

DHA is required for the optimal development of the nervous system and maturation of visual acuity in preterm and full term infants. DHA is the most highly unsaturated fatty acid found in nature and the predominant structural fatty acid in the brain (40%) and retina (60%). It was also shown to have significant effects at the auto-immune system.

ETA are a unique family involved in joint inflammation prevention and treatment. They act as potent nutritional inhibitors of the lipoxygenase pathway, which are responsible for leukotrienes production.

Other products comprise MCT (Medium chain triglycerides: C6, C8 and C10) that are involved in the reduction of mortality of premature new born infants weighing <1.5 Kg or piglets during the weaning age.

Omega-3 fatty acids and MCT have in common the fact they are all in oil form. It has been proposed to stabilise these lipids so as to produce and protect marine oils for food fortification use (bakery products, milk powder). There has been suggestion of incorporating into soft gel capsules for the health products market.

The Calcium Product of the invention offers an unusually effective alternative to the above techniques of presentation because of its highly porous structure. This highly porous structure provides a high specific structure on the same particle size of 9 m² as against 1.7 m² for calcium carbonate in more conventional forms. This porous structure can be demonstrated using a scanning electron microscopic technique. The Calcium Product of the invention allows the possibility of combining with the above lipid products without affecting the particle size or the flowability of the final product. The precise relationship will depend on the nature of the lipid compound and the molecular weight which bears upon the relationship to the pore size of the Calcium Product.

The products have a neutral taste (probably because of the absorption into the pores of the Calcium Product. Absorption of 5 to 15% by weight gives a very useful product.

Thus the product of the invention provides the possibility of a combination of MCT and a calcium product as a calcium source for baby food. Also there is provided the possibility of a combination of omega-3 LCFA's (EPA, DHA and DTA) as a calcium source for food fortification intended for children and adults.

Combinations of the invention comprising the Lithothamnium corallioides residues (the Calcium Product) and MCT's are particularly of interest.

Generally fats, or lipids, perform a variety of functions including energy storage, membrane structure and incorporation in vitamins, hormones and prostaglandins. Triglycerides are the most common form of fat. Triglycerides comprise three fatty acids esterified to a glycerol backbone. Most naturally occurring triglycerides contain fatty acids 16–20 carbon atoms in length. Such fatty acids are called "long chain fatty acids" (LCFAs), and their corresponding triglycerides are called "long chain triglycerides" (LCTs). Medium chain triglycerides (MCTs) comprise medium chain fatty acids (MCFAs), which are 6–12 carbons in length. Although the carboxylic acid part of fatty acids is soluble in water, the hydrocarbon chain is not. Thus, LCFAs are not water soluble. Since the hydrocarbon chains of MCFAs are shorter, MCFAs are more water soluble than LCFAs. Likewise, MCTs are also relatively soluble in water, due to ionization of the carboxylic acid groups and the small size of the hydrocarbon chains. Their small molecular size and greater water solubility cause MCTs to undergo a different metabolic path than that experienced by LCTs.

Medium chain triglycerides occur naturally in small quantities in a variety of foods, including human milk. In cow's milk, C6–C14 fatty acids together account for 20% of the total fatty acid composition. Commercially medium chain fatty acids are prepared by the hydrolysis of coconut oil and fractionate up by steam distillation. The MCFAs so obtained consist of predominantly C8 with lesser amounts of C10 and minute amounts of C6 and C12. The fractionated MCFAs can be re-esterified with glycerol to generate MCTs.

MCTs have been used for fat malabsorption problems and have been widely used in enteral and parenteral nutrition. Use of the MCT's permits provision of calories in a more readily oxidisable form and less interference with the RES component of the immune system. Recently athletes have begun to use MCT's to provide energy and facilitate weight gain.

In metabolism the solubility of the MCFA's avoids a complicated digestive process found with LCT's. The MCT's are readily degraded within the intestine into free MCFA's and glycerol. Therefore as compared to conventional fats MCT's are transported directly to the liver and used for energy rather than being stored in cells. This indicates the desirability of MCT's as components of foodstuffs to avoid deposition of fats. MCT's therefore have been incorporated into diets particularly for sports persons. An example is the interest in goats milk which contains higher content of MCT's as compared to cow milk.

Thus capric, caprylic and other MCT's have been used for the treatment of malabsorption syndrome, intestinal disorders, coronary diseases, premature infant nutrition, cystic fibrosis and gallstone problems because of the capacity to provide energy and possibly dissolve cholesterol deposits. Similarly coconut products, particularly coconut oil which is an excellent source of medium-chain triglycerides has received much attention.

Methods of incorporating MCT's more effectively into the diet by combination with absorbants are therefore of considerable interest and the discovery that the Calcium Product of the invention affords a excellent means of absorbing MCT's is of great significance.

Another aspect of the invention is the combination of the Calcium Product with polyols such as glycerol, monopropylene glycol and viscous polyols alone or with other functional products. Such products comprising a combination of a monoglyceride and the Calcium Product of the invention could be a calcium source for bakery products, bread, toppings, margarine and spreads, chocolates and all calcium fortification products employing monoclycerides as emulsifiers. Combining Calcium Product with emulsifiers, particularly glycerides, would provide a new range of products for calcium fortification and emulsification. The emulsifiers are preferably those having properties analogous to glycerides but the invention applies to emulsifiers used in the food industry particularly to stabilise oil/water emulsions.

The combination of the Calcium Product and polyols, glycols, mono-or di-glycerides and emulsifiers generally simplifies the introduction of the emulsifier. It has been found that, if the emulsfier is incorporated into the Calcium Product and simultaneously or subsequently with an "oil phase" the formation thereafter of an emulsion with an aqueous phase gives an improved emulsion of greater stability.

The combination of the calcium product and the fatty acid or polyol can be carried out by any of the standard techniques for combining solid carrier and materials such as fatty acids, glycerides and polyols. It is preferred to use one of the following techniques:

Air Suspension Coating, known also as fluidised bed processing or spray coating. The bed is sprayed with a coating solution. The coating dries on the core powder to form a film of a certain thickness.

Spray chilling and Spray Cooling; The coating substance can be a derivative of vegetable or other encapsulating materials, i.e. stearine with melting points of 45° C. to 122° C. as well as mono and diglycerides with melting points of 45° C. to 67° C. The coated material is obtained by nebulising the coating substance with heated nozzles into a chamber containing cool air. The reduction of temperature results in solidification of the lipid coat.

Differential Scanning Calorimetry (DSC) can be used to monitor changes in physical or chemical properties of materials as a function of temperature by detecting the heat changes associated with such processes.

BRIEF DESCRIPTION OF THE DRAWINGS

The invention is illustrated by the accompanying drawings in which.

☐Size μm 0 R
◇Size μm 5 R
○Size μm 10 R
ΔSize μm 12 R
⊞ μm 15 R

☐Size μm 0 R
◇Size μm 5 S
○Size μm 10 S
ΔSize μm 12 S
⊞ μm 15 S

☐Size μm Control
◇Size μm 5% S R
○Size μm 10% S R
ΔSize μm 10% MG1 R
⊞ μm 10% FA R
◆Size μm 10% MG2 R
●Size μm 10% TG1 R
▽Size μm 10% TG2 R The particle sizes in FIG. 4 are represented by the following symbols:
☐Size μm Control
◇Size μm 5% S S
○Size μm 10% S S
ΔSize μm 10% MG1 S
⊞ μm 10% FA S
◆Size μm 10% MG2 S
●Size μm 10% TG1 S
▽Size μm 10% TG2 S

☐Size μm Aquacal
◇Size μm CaCO3
⊞ Size μm CaCO3 coated R
ΔSize μm Aquacal coated R The particle sizes in FIG. 6 are represented by the following symbols:
☐Size μm Aquacal
◇Size μm CaCO3
○Size μm CaCO3 coated S1
ΔSize μm CaCO3 coated S2
■Size μm Aquacal coated S

DETAILED DESCRIPTION OF PREFERRED EMBODIMENTS

The Calcium Product employed is a commercial product prepared from Lithothamnium corallioides residues as described above and having the analysis set out above.

More than 300 human volunteers were found and dosed three times a day with capsules containing 0.5 grammes of purified concentrate of Lithothamnium corallioides residue from dredging at Lonehort Point.

Some of the results are reported in the following Example.

EXAMPLE 1

One group of volunteers suffered from rheumatoid and osteo arthritis.

It was found that depending on age, greatly improved mobility was experienced with the above daily consumption preferably with meals. Younger patients experienced relief within 3 weeks, whereas older patients and particularly those in the 70/80 age bracket took 8/12 weeks to show substantial improvement.

Once achieved, daily consumption was necessary to ensure maintenance of enhanced mobility.

EXAMPLE 2

Another group of volunteers suffered from gout. These volunteers were dosed in the same way as above.

It was found that complete elimination of gout symptoms occurred within a few days of use in 90% of trial participants.

From laboratory results it appears that the uric acid is maintained in a molecular condition, which precludes deposition.

EXAMPLE 3

A further group of volunteers were dosed as above. Cholesterol levels were found to have been reduced with a drop from for example 6.8/7.5 to 5.2/5.4 being possible in about 40% of subjects.

EXAMPLE 4

A further group of volunteers were dosed as above. It was found that period pains could be totally eliminated and that premenstrual tension could be reduced.

EXAMPLE 5

Patients were dosed as above and it was shown that body fluid pH (as determined by salivary pH levels) could be adjusted to and maintained at 6.8–7.0 which is the generally accepted optimum body fluid pH.

EXAMPLE 6

Patients were dosed as above and it was shown that indole and sulphite residues were eliminated in the urine.

EXAMPLE 7

Patients were dosed as above and it was shown there was a lowering of triglyceride levels in the blood.

EXAMPLE 8

Patients were dosed as above and it was shown there was an increase in urine production i.e. that there was water diuresis result (dehydration).

Compositions Comprising Purified Residue in Lithothamnium Corallioides

EXAMPLE 9

Combination with Medium Chain Triglycerides (MCT)

MCT is a low viscous oil, almost colourless from caprylic (C8) and capric (C10) vegetable fatty acids.

A Calcium Product was prepared by purification of Lithothamnium corallioides harvested at Loenhort Point described above (Calcium Product).

Initial trial work showed that Calcium Product maximum oil absorption capacity was 64%. At this level the flowability was lost, the product being in the paste form. The optimum level of MCT absorption compatible with flowability using an air suspension coating technique was readily determinable.

Calcium Product was coated with 5%, 10%, 12% and 15% MCT.

Figure 1:
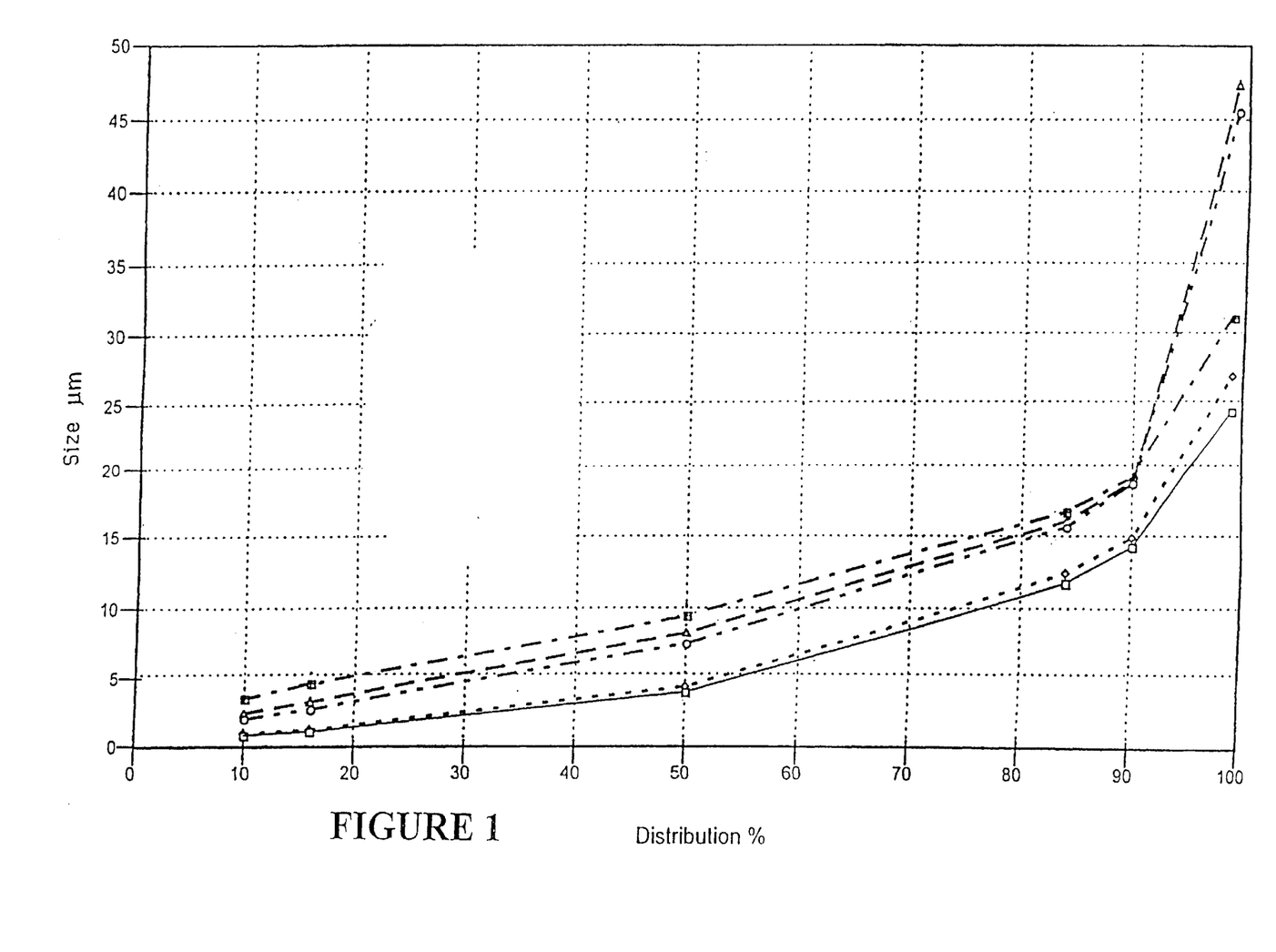
FIG. 1 is a distribution of the particle sizes on the introduction of MCT measured on a "HELOS" (Trade Name) laser particle size determination apparatus (Example 9), i.e. analysis on dry form of coated "Calcium Product" with 0%; 5%; 10%; 12% and 15% MCT. The particle sizes are represented in FIG. 1 by the following symbols.

FIG. 1 shows a regular increase of the particles size according to the level of MCT, below 90% distribution. Above 90% there is a derivation due to some aggregates (analysis of non sieved coated product). This is confirmed by FIG. 2 on wet product analysis: the aggregates are disrupted. Globally, the particles size remain below 3 μm.

Figure 2:
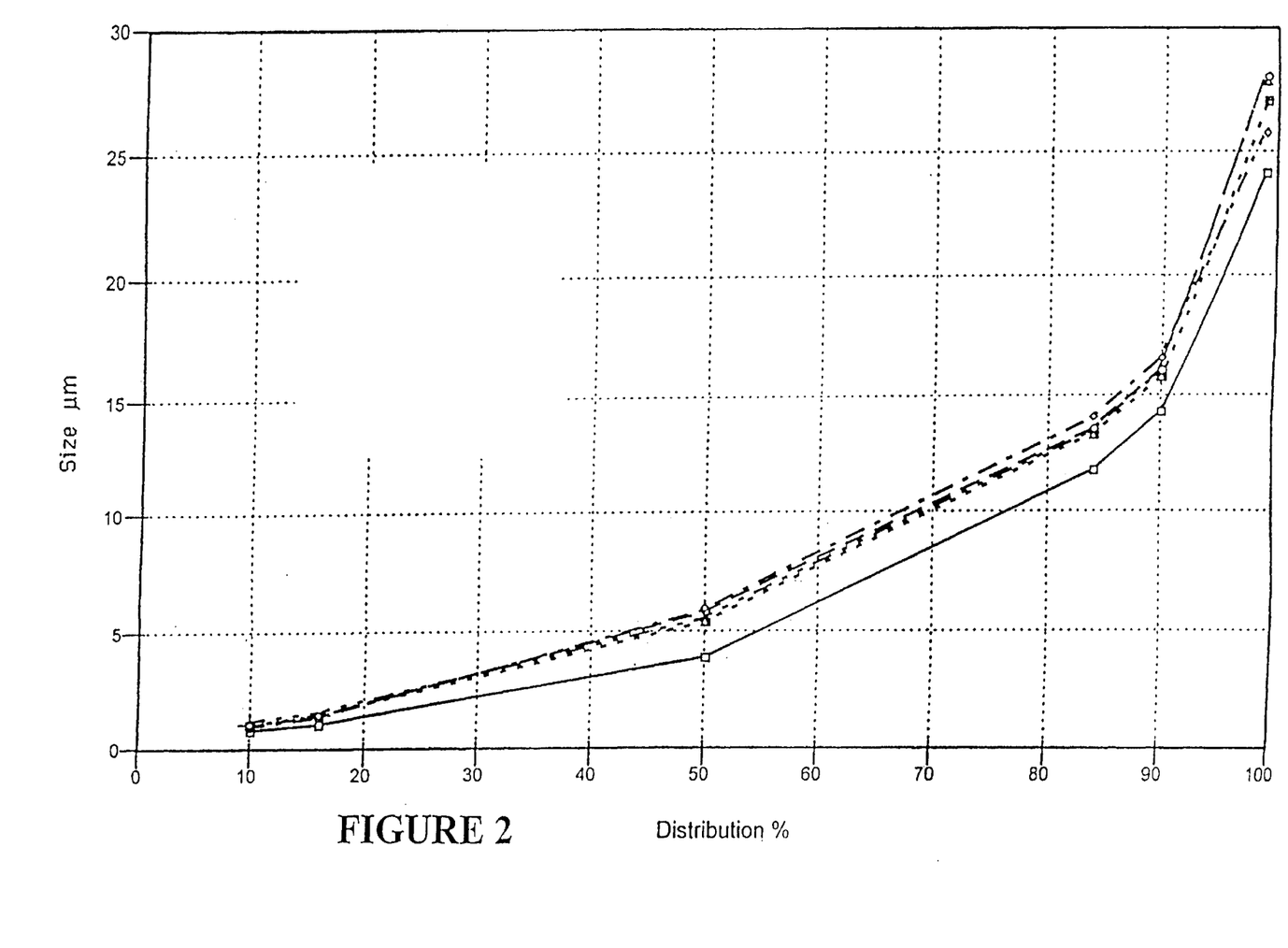
FIG. 2 is a "HELOS" laser particle size analysis on wet form of coated "Calcium Product" with 0%; 5%; 10%; 12% and 15% MCT (Example 9). The particle sizes are represented in FIG. 2 by the following symbols.

The 5% coating gave 2 density peaks close to those of the control. The coating was not obviously sufficient to agglomerate the finest particles. From 10 to 15% coating there was a unique density peak.

EXAMPLE 10

Tests with Different Emulsifiers

A Calcium Product as described above was combined with various emulsifiers as follows:

| Emulsifier | Melting Point ° C. | Sample Nos. |
|---|---|---|
| Sorbitan | 20 | (1) 5% (2) 10% |
| Monoglyceride 1 | 35–40 | 3 |
| Fatty Alcohol | 55–58 | 4 |
| Monoglyceride 2 | 68–70 | 5 |
| Triglyceride 1 | 52–53 | 6 |
| Triglyceride 2 | 58 | 7 |

The samples were coated at 10% by weight except for Sorbitan: 5% and 10%.

Figure 3:
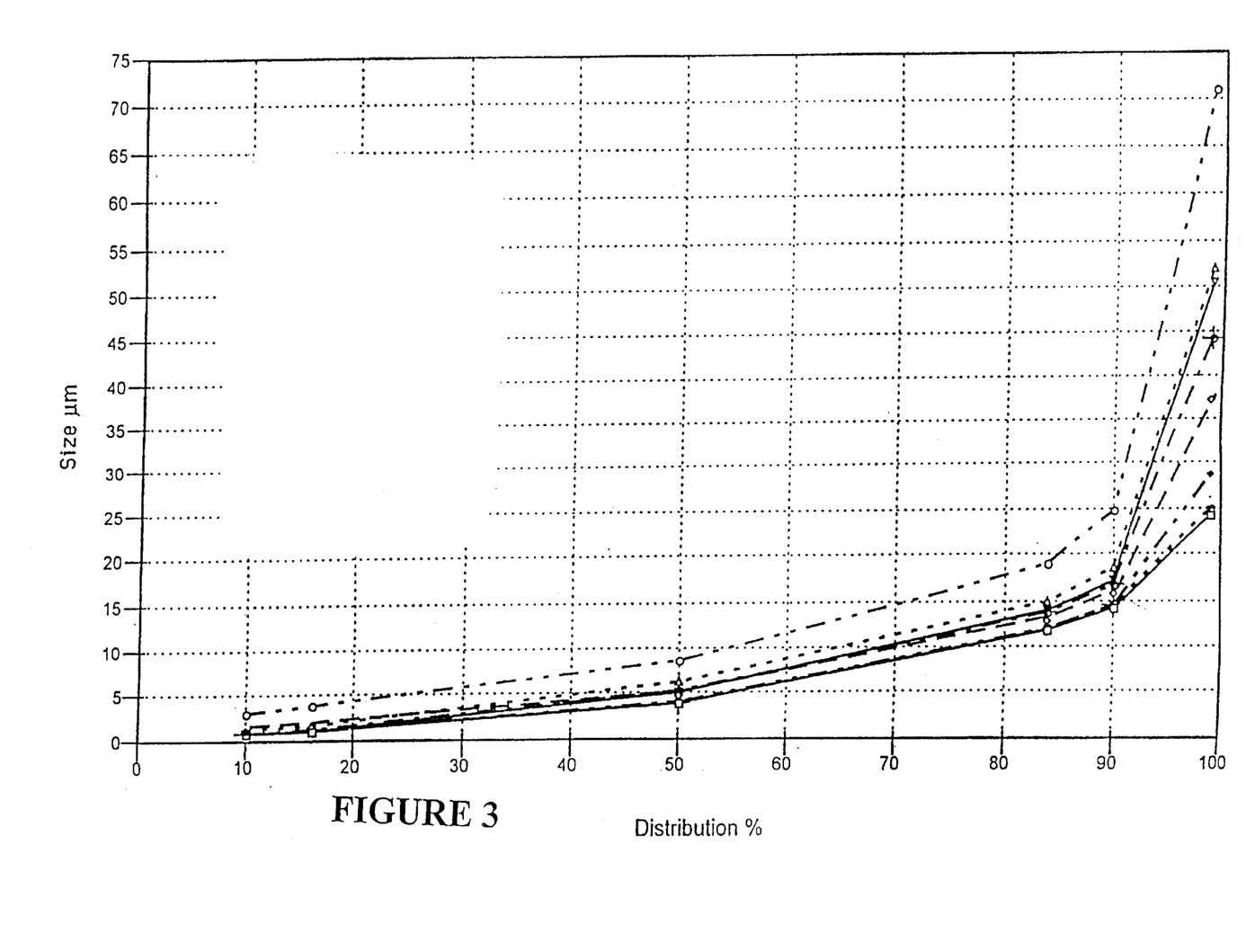
FIGS. 3 and 4 illustrate "HELOS" laser particle size analysis on dry or wet form, respectively, of coated "Calcium Product" with 10% emulsifier (and 5% for sorbitan) (Example 10). The particle sizes in FIG. 3 are represented by the following symbols.
Figure 4:
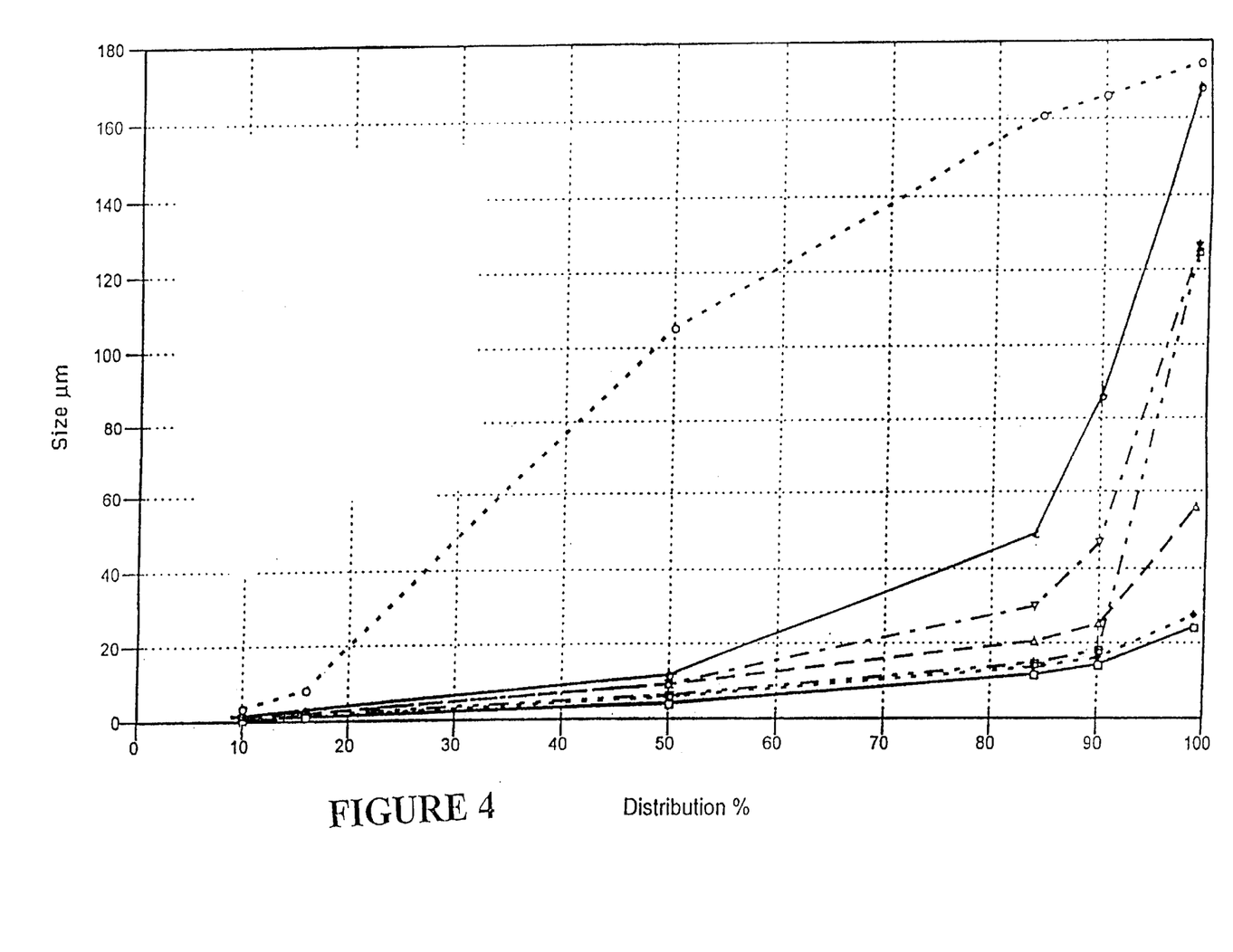

The analysis were done again on the non sieved treated products. The most flowable ones were with the 2 monoglycerides. The laser particles size analysis do not clearly reveal that point (FIGS. 3 & 4) except for FIG. 4 on wet form.

The DSC analysis results clarify the interaction between the tested emulsifiers and Calcium Product.

Calcium Product coated samples were analysed by DSC in the range of temperature 5 to 125° C. using a rate of heating of 5° C./min. A first series of data were obtained in these conditions. Results are shown in Table 1.

TABLE 1

| | Glass Transition | | Melting | | | | | | Recrystal |
|---|---|---|---|---|---|---|---|---|---|
| | | | Melting 1 | | | Melting 2 | | | |
| | Tg1 | Tg2 | $T_m$onset 1 | $T_m$ peak 1 | ΔHf1(J/g) | $T_m$ onset 2 | $T_m$ peak 2 | ΔHf2 (J/g) | Tr |
| 1 | | 53.54 | | | | | | | |
| 2 | | 26.77 | 36.88 | | | | | | |
| 3 | | 24.34 | | 32.34 | 35.3 | −2.494 | | | 20 |
| 4 | | 50.61 | | 61.06 | 63.1 | −5.984 | | | 45 |
| 5 | | 39.78 | | 68.43 | 71.4 | −2.674 | | | 35.5 |
| 6 | | 31.27 | | 51.07 | 56.4 | −4.494 | | | 26.7 |
| 7 | | | | 50.57 | 53.7 | −3.789 | 58.47 | 62.4 | −4.577 |

Thermograms were interpreted as melts when the endothermal peaks of melting are well defined with an onset and a peak temperature of melting. Glass transitions (Tg) were also derived from the thermograms showing a change in heat flow with a slope of baseline unchanged. Some samples show polymorphism behaviour with 2 melting endotherms. When an endotherm is observed it is assigned to a recrystallisation.

In a second series of analyses all samples were heated rapidly (10° C./Min) to 120° C., then cooled rapidly to −10° C. DSC analysis was performed on these annealed samples at a rate of 5° C./min. Results are shown in Table 2.

TABLE 2

| | Glass Transition | | Melting | | | | | | Recrystal |
|---|---|---|---|---|---|---|---|---|---|
| | | | Melting 1 | | | Melting 2 | | | |
| | Tg1 | Tg2 | $T_m$onset 1 | $T_m$peak 1 | ΔHf1(J/g) | $T_m$ onset 2 | $T_m$ peak 2 | ΔHf2 (J/g) | Tr |
| 1 | | 41.41 | | | | | | | |
| 2 | | 38.88 | | | | | | | |
| 3 | | | | 22.1 | 27.1 | | | | |
| 4 | | 23.52 | 54.68 | 59.78 | 61.8 | −2.698 | | | 19.1 |

TABLE 2-continued

| | Glass Transition | | Melting 1 | | | Melting 2 | | Melting | Recrystal |
|---|---|---|---|---|---|---|---|---|---|
| Tg1 | Tg2 | T$_m$onsel 1 | T$_m$peak 1 | ΔHfl(J/g) | T$_m$ onset 2 | T$_m$ peak 2 | ΔHf2 (J/g) | | Tr |
| 5 | | | 67.74 | 70.9 | −5.308 | | | | |
| 6 | | | 49.67 | 56 | −4.264 | | | | |
| 7 | | | 50.22 | 52.9 | −3.245 | 58.51 | 62 | −3.99 | |

It may be observed that erasing the thermal history of samples by annealing eliminates a number of pseudo-thermal events, especially as concerns Tg and recrystallisation. The polymorphism of a product containing triglyceride 2 was confirmed and the melting points of different samples was verified, except for monoglyceride 1 which showed an endotherm at lower temperature (22–27° C.) after annealing than before. This indicates a unique interaction between Calcium Product and low melting point monoglyceride.

Monoglycerides gave good themograms and the coated materials were free flowing, which was not the case with the other products.

EXAMPLE 11

Comparison Between Calcium Product and Calcium Carbonate

A Calcium Carbonate was employed from a normal commercial source.

The Calcium Product of the invention and Calcium Carbonate were coated with 10% monoglyceride-1.

Figure 5:
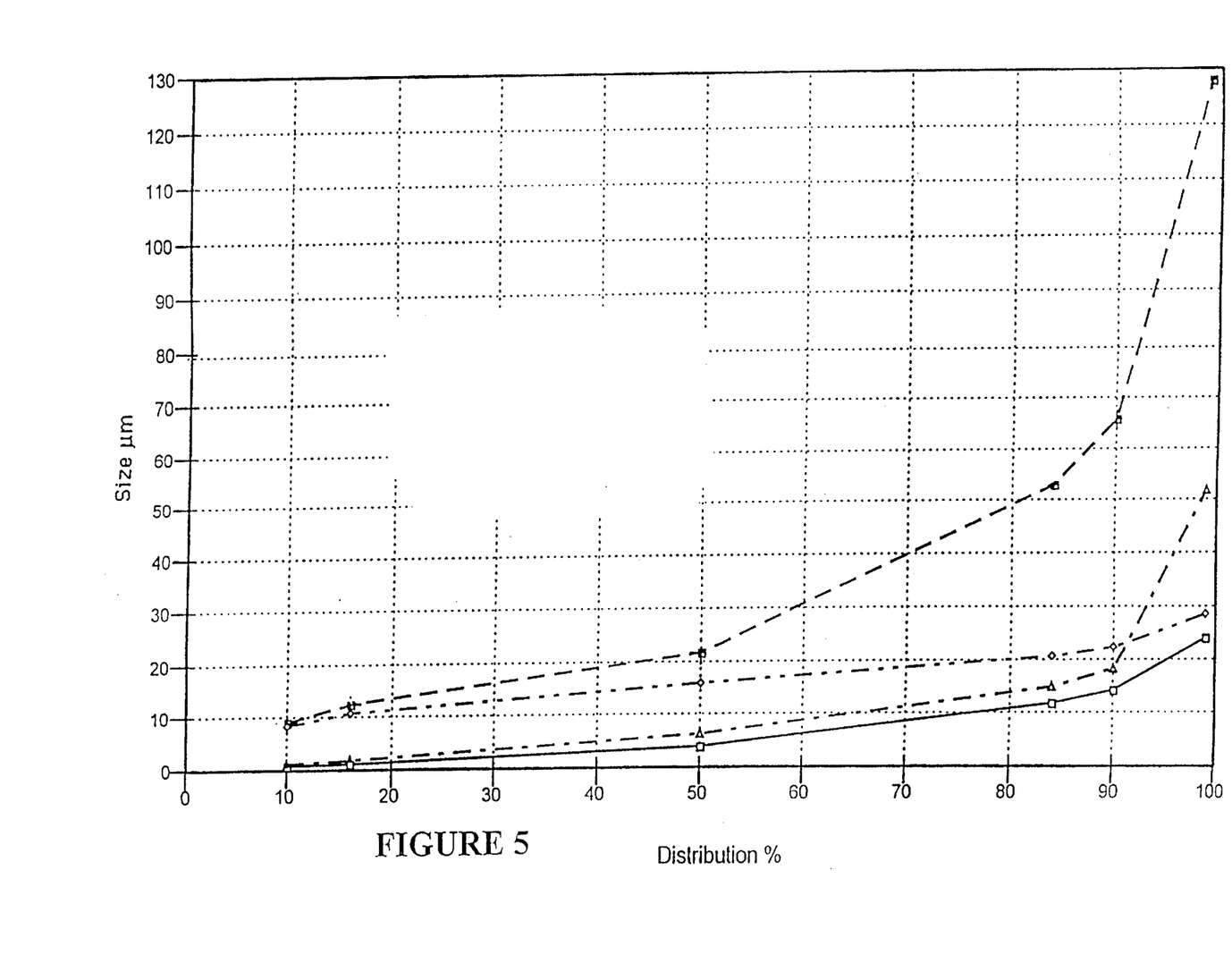
FIGS. 5 and 6 illustrate "HELOS" laser particle size analysis on dry or wet form, respectively, of coated "Calcium Product" and CaCo₃ with 10% Monoglyceride (MP:35–40° C.). The particle sizes in FIG. 5 are represented by the following symbols.

The coating was done with 10% monoglyceride-1. Calcium Product gave a homogeneous product. The taste was neutral and corresponded to that of the original Calcium Product. Calcium carbonate gave a heterogeneous product, non flowable and produced large particles (FIG. 5). The taste was chalky and also revealed the typical emulsifier taste. This is an indication of the presence of three populations: Calcium Carbonate (pure and coated) and free emulsifier.

The wet form analysis (FIG. 6) revealed the presence of fine particles below 8 μm. These come from the crystallised emulsifier. The distribution curve recovers its initial form from 50%. It shows a complete separation between the emulsifier and the carrier. The absence of porosity explains the behaviour of calcium carbonate with monoglyceride.

Figure 6:
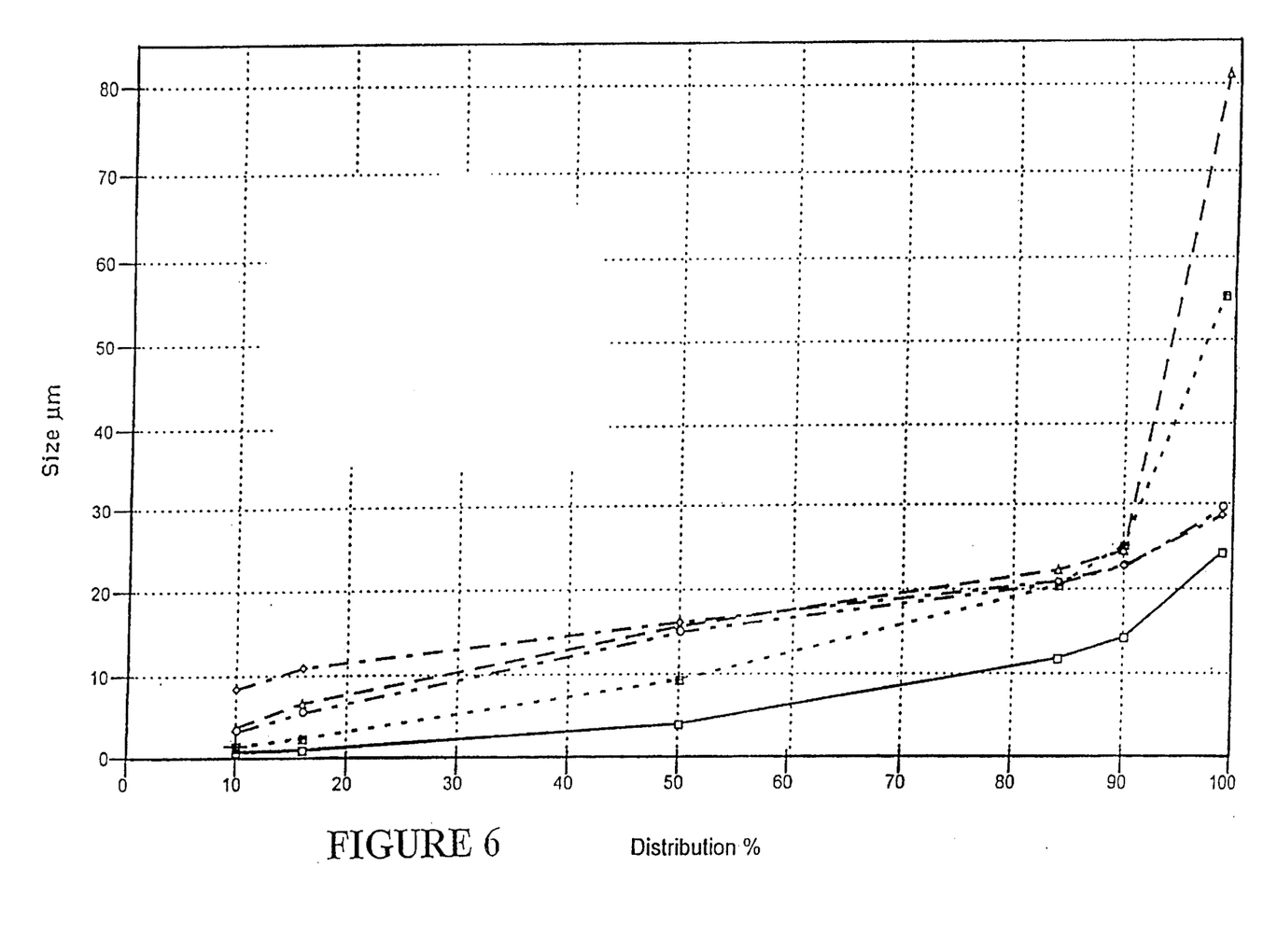

Calcium Product gave a completely different figure with the curve of the coated material remaining above the control.

What is claimed is:

1. A medicament for the treatment of conditions created by a failure of immuno regulation in the body comprising the residue of corallinaceae which has been purified to reduce the sodium content of the raw material of corallinaceae residue by at least 10 fold as compared to that raw material.

2. Medicament according to claim 1, wherein the corallinaceae residue is the residue of Lithothamnium coralliodes.

3. Medicament according to claim 1, in which the sodium content is reduced into the low hundreds ppm by weight.

4. Medicament according to claim 1, in which the silica content of the residue has reduced to about 0.5% or less by weight.

5. A method of forming a form of corallinaceae for medical treatment of human or animals in which siliceous materials and debris are removed from a dredged product, the product is intensively washed, then the product is bleached, cleansed and sterilised particularly by hydrogen peroxide, the purification being sufficient to reduce the content of sodium as compared to the raw material by at least 10 fold, and dried and packaged under sterile conditions.

6. A method according to claim 5, wherein the sterilisation is by application of hydrogen peroxide.

7. A composition comprising the combination of a residue of a corallinaceae (Maërl) which has been purified to lower the sodium content of the raw material by at least 10 fold and a fatty acid, a glyceride or a polyglycol.

8. A composition comprising the combination of a residue of a corallinaceae (Maërl) which has been purified to lower the sodium content of the raw material by at least 10 fold and an emulsifier.

9. A composition according to claim 7, in which the residue is the residue of Lithothamnium corallioides.

10. A composition according to claim 8, in which the residue is the residue of Lithothamnium corallioides.

11. A composition according to claim 7, wherein the fatty acid is a functional polyunsaturated fatty acid.

12. A composition according to claim 11, wherein the acid is arachidonic acid (ARA), eicosapentaenoic acid (EPA), docosahexaenoic acid (DHA) and eicosatetraenoic acid (ETA).

13. A composition according to claim 7, in which glyceride is a medium chain trigiyceride of 6 to 10 carbon atoms.

14. A composition according to claim 7, in which the polyol is glycerol or monopropylene glycol.

15. A method of forming emulsions in the manufacture of foods wherein an emulsifier is combined with a residue of corallinaceae (Maërl) which has been purified to reduce the sodium content of the raw material of corallinaceae residue by at least 10 fold as compared to that raw material and simultaneously or subsequently with an oil phase of a food stuff and thereafter an emulsion is formed with an aqueous phase.

16. A method for forming an emulsion in the manufacture of margarine wherein a monoglyceride is combined with a residue of corallinaceae (Maërl) which has been purified to reduce the sodium content of the raw material of corallinaceae residue by at least 10 fold as compared to that raw material and simultaneously or subsequently with an oil phase for a margarine and thereafter an emulsion is formed with an aqueous phase.

17. A method for treating the condition of artritis in a patient comprising administering to the patient an effective amount of the medicament of claim 1 to treat the condition.

18. A method for treating the condition of gout in a patient comprising administering to the patient an effective amount of the medicament of claim 1 to treat the condition.

19. A method for treating the condition raised cholesterol levels in a patient comprising administering to the patient an effective amount of the medicament of claim 1 to treat the condition.

20. A method for treating the condition of period pains in a patient comprising administering to the patient an effective amount of the medicament of claim 1 to treat the condition.

21. A method for treating the condition of osteoporosis in a patient comprising administering to the patient an effective amount of the medicament of claim 1 to treat the condition.

22. A method for treating the condition of chronic fatigue in a patient comprising administering to the patient an effective amount of the medicament of claim 1 to treat the condition.

23. A method for treating a condition created by reduced body fluid pH level in a patient comprising administering to the patient an effective amount of the medicament of claim 1 to treat the condition.

24. A method for treating an incipient ulcerative condition in a patient comprising administering to the patient an effective amount of the medicament of claim 1 to treat the condition.

25. A method for treating the condition of indigestion in a patient comprising administering to the patient an effective amount of the medicament of claim 1 to treat the condition.

26. A method for treating the condition of reduce calcium levels in a patient comprising administering to the patient an effective amount of the medicament of claim 1 to treat the condition.

27. A method for treating the condition of a hangover in a patient comprising administering to the patient an effective amount of the medicament of claim 1 to treat the condition.

28. A method for raising pH levels in the colon of a patient comprising administering to the patient on effective amount of the medicament of claim 1 to raise the pH levels.

* * * * *